(12) United States Patent
Ankersen

(10) Patent No.: US 6,576,648 B2
(45) Date of Patent: *Jun. 10, 2003

(54) COMPOUND WITH GROWTH HORMONE RELEASING PROPERTIES

(75) Inventor: Michael Ankersen, Stenlose (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 09/817,840

(22) Filed: Mar. 26, 2001

(65) Prior Publication Data

US 2001/0041720 A1 Nov. 15, 2001

Related U.S. Application Data

(63) Continuation of application No. PCT/DK00/00624, filed on Nov. 10, 2000.
(60) Provisional application No. 60/167,101, filed on Nov. 23, 1999.

(30) Foreign Application Priority Data

Nov. 10, 1999 (DK) .......................... 1999 01618

(51) Int. Cl.$^7$ ..................... A61K 31/445; C07D 401/00
(52) U.S. Cl. ....................................... 514/323; 546/201
(58) Field of Search ........................... 514/323; 546/201

(56) References Cited

U.S. PATENT DOCUMENTS

| 5,492,916 A | 2/1996 | Morriello et al. ............ 514/318 |
| 5,622,973 A | 4/1997 | Morriello et al. ............ 514/318 |
| 5,721,250 A | 2/1998 | Morriello et al. ............ 514/318 |
| 6,303,620 B1 * | 10/2001 | Hansen et al. ............... 514/278 |
| 2001/0020012 A1 * | 9/2001 | Andersen et al. ............. 514/46 |

FOREIGN PATENT DOCUMENTS

| WO | WO 88/09780 | 12/1988 |
| WO | WO 89/07110 | 8/1989 |
| WO | WO 89/10933 | 11/1989 |
| WO | WO 91/18016 | 11/1991 |
| WO | WO 92/01711 | 2/1992 |
| WO | WO 93/04081 | 3/1993 |
| WO | WO 95/14666 | 6/1995 |
| WO | WO 99/36431 | 7/1999 |
| WO | WO 99/58501 | 11/1999 |

* cited by examiner

Primary Examiner—Ceila Chang
(74) Attorney, Agent, or Firm—Cheryl H. Agris; Reza Green

(57) ABSTRACT

The present invention describes a new compound, 2-Amino-N-[(1R)-2-[(3R)-3-benzyl-3-(N,N',N'-trimethylhydrazinocarbonyl)piperidin-1-y]-1-(1H-indol-3-ylmethyl)-2-oxoethyl]-2-methylpropionamide, having the formula:

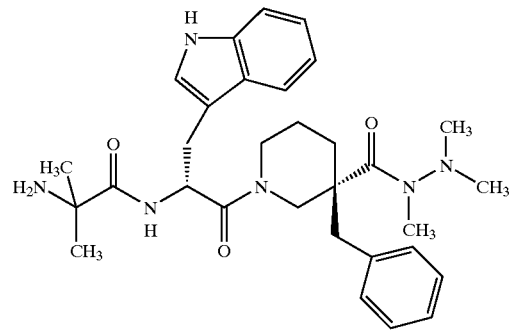

and pharmaceutically acceptable salts thereof, compositions containing them, and their use for treating medical disorders resulting from a deficiency in growth hormone.

4 Claims, No Drawings

COMPOUND WITH GROWTH HORMONE RELEASING PROPERTIES

CROSS REFERENCE TO RELATED APPLICATIONS

This application is a continuation of PCT/DK00/00624 filed on Nov. 10, 2000, and claims priority under 35 U.S.C. 119 of Danish application no. PA 1999 01618 filed on Nov. 10, 1999, and U.S. provisional application Ser. No. 60/167,101 filed on Nov. 23, 1999, the contents of which are fully incorporated herein by reference.

FIELD OF INVENTION

The present invention relates to a new compound, pharmaceutically acceptable salts thereof, compositions containing them, and their use for treating medical disorders resulting from a deficiency in growth hormone.

BACKGROUND OF THE INVENTION

Growth hormone is a hormone, which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred.

The use of certain compounds for increasing the levels of growth hormone in mammals has previously been proposed, e.g. in EP 18 072, EP 83 864, WO 8302272, WO 8907110, WO 8901711, WO 8910933, WO 8809780, WO 9118016, WO 9201711, WO 9304081, WO 9413696, WO 9517423, WO 9514666, WO 9615148, WO 9622997, WO 9635713, WO 9700894, WO 9722620, WO 9723508, WO 9740023, and WO 9810653.

The composition of growth hormone releasing compounds is important for their growth hormone releasing potency as well as their bioavailability. It is therefore an object of the present invention to provide a novel compound with growth hormone releasing properties. Moreover, it is an object to provide a novel growth hormone releasing compound (growth hormone secretagogue) which are specific and/or selective and have no or substantially no side-effects, such as e.g. release of LH, FSH, TSH, ACTH, vasopressin, oxytocin, cortisol and/or prolactin. It is also an object to provide a compound which has a good oral bioavailability.

SUMMARY OF THE INVENTION

In accordance with the present invention there is provided a novel compound which act directly on the pituitary cells under normal experimental conditions in vitro to release growth hormone therefrom.

The growth hormone releasing compound can be utilized in vitro as unique research tools for understanding, inter alia, how growth hormone secretion is regulated at the pituitary level.

Moreover, the growth hormone releasing compound of the present invention can also be administered in vivo to increase endogenous growth hormone release.

DESCRIPTION OF THE INVENTION

Accordingly, the present invention relates to a new compound 2-Amino-N-[(1R)-2-[(3R)-3-benzyl-3-(N,N',N'-trimethylhydrazinocarbonyl)piperidin-1-yl]-1-(1H-indol-3-ylmethyl)-2-oxoethyl]-2-methylpropionamide, having the following chemical structure

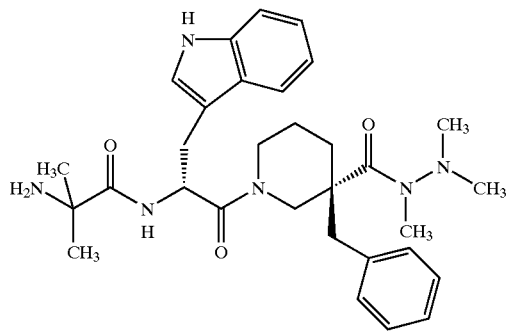

or a pharmaceutically acceptable salt thereof.

Furthermore, the present invention relates to the compound 2-Amino-N-[(1R)-2-[(3R)-3-benzyl-3-(N,N',N'-trimethylhydrazinocarbonyl)piperidin-1-yl]-1-(1H-indol-3-ylmethyl)-2-oxoethyl]-2-methylpropionamide

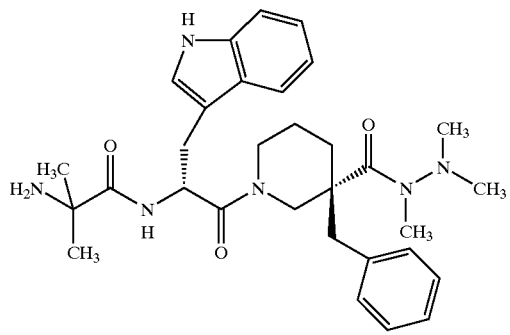

or a pharmaceutically acceptable salt thereof.

The structure of the compound obtainable by the procedure as described in example 1 can e.g. be verified by X-ray diffraction analysis (e.g. as described in Remington: The Science and Practice of Pharmacy, 19th Edition (1995), especially pages 160 and 561–562).

Any possible combination of two or more of the embodiments described herein is comprised within the scope of the present invention.

Synthetic Methods in General

The procedure used in this patent is based on peptide couplings well known in the art, and should in no way be interpreted as limiting the invention in any way.

In the procedure, prior to a coupling of amino acid or peptide residues, a suitable protecting group such as tert butyloxycarbonyl (Boc) can be removed with methods well known to those skilled in the art. It is also possible to avoid the use of protecting groups. The appropriate amino acids may be protected and deprotected by methods known in the art and described by e.g. T. W. Green (Protective Groups in Organic Synthesis, 2. Ed., John Wiley and Sons, New York 1991).

Example 1 describes the procedure in details. By resolution of the racemic mixture of 3-benzylpiperidine-1,3-dicarboxylic acid 1-tert-butyl ester to obtain one of the enantiomeric compounds, the final compound obtained by the procedure is the diastereomer 2-Amino-N-[(1R)-2-[(3R)-3-benzyl-3-(N,N',N'-trimethylhydrazinocarbonyl)piperidin-1-yl]-1-(1H-indo-3-ylmethyl)-2-oxoethyl]-2-methylpropionamide

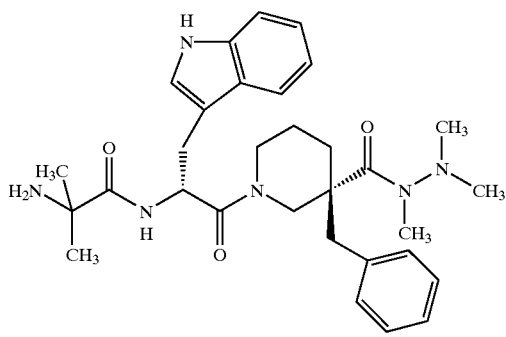

instead of the mixture of the two diastereomers.

The compound of the present invention exhibits an improved resistance to proteolytic degradation by enzymes because it is non-natural, in particular because the natural amide bonds are replaced by non-natural amide bond mimetics. The increased resistance to proteolytic degradation of the compound of the invention in comparison with known hormone releasing peptides is expected to improve its bioavailability compared to that of the peptides suggested in the prior literature.

Pharmaceutical Composition

The compound of the present invention may optionally be on a pharmaceutically acceptable salt form such as the pharmaceutically acceptable acid addition salts of the compounds of the present invention which include those prepared by reacting the compound of formula I with an inorganic or organic acid such as hydrochloric, hydrobromic, sulfuric, acetic, phosphoric, lactic, maleic, mandelic phthalic, citric, glutaric, gluconic, methanesulfonic, salicylic, succinic, tartaric, toluenesulfonic, trifluoracetic, sulfamic or fumaric acid and/or water.

The compound of the present invention may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the present invention or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences,* 1985 or in Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 10 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of the present invention dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 0.01–500 mg/day, e.g. from about 5 to about 50 mg, such as about 10 mg per dose, when administered to patients, e.g. humans, as a drug.

In a further aspect the present invention relates to a pharmaceutical composition in unit dose form, comprising as an active ingredient from about 10 to about 200 mg of the compound of the general formula I or a pharmaceutically acceptable salt thereof.

It has been demonstrated that the compound of the present invention possess the ability to release endogenous growth hormone in vivo. The compound may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the present invention or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the present invention or a pharmaceutically acceptable salt thereof.

In a still further aspect, the present invention relates to the use of a compound of the present invention or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, the compound of the present invention can be administered for purposes stimulating release of growth hormone from the pituitary and would then have similar effects or uses as growth hormone itself. The compounds of the present invention is useful for: stimulation of growth hormone release in the elderly, prevention of catabolic side effects of glucocorticoids, prevention and treatment of osteoporosis, treatment of chronic fatigue syndrome (CFS), treatment of acute fatigue syndrome and muscle loss following elective surgery, stimulation of the immune system, acceleration of wound healing, accelerating bone fracture repair, accelerating complicated fractures, e.g. distraction osteogenesis, treatment of wasting secondary to fractures, treatment of growth retardation, treating growth retardation resulting from renal failure or insufficiency, treatment of cardiomyopathy, treatment of wasting in connection with chronic liver disease, treatment of thrombocytopenia, treatment of growth retardation in connection with Crohn's disease, treatment of short bowel syndrome, treatment of wasting in connection with chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; increasing the growth rate of a patient having partial growth hormone insensitive syndrome, accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of catabolism in connection with pulmonary dysfunction and ventilator dependency; treatment of cardiac failure or related vascular dysfunction, treatment of impaired cardiac function, treatment or prevention of myocardial infarction, lowering blood pressure, protection against ventricular dysfunction or prevention of reperfusion events; treatment of adults in chronic dialysis; attenuation of protein catabolic responses after major surgery, reducing cachexia and protein loss due to chronic illness such as cancer or AIDS; treatment of hyperinsulinemia including nesidioblastosis, adjuvant treatment for ovulation induction; stimulation of thymic development and prevention of the age-related decline of thymic function, treatment of immunosuppressed patients; treatment of sarcopenia, treatment of wasting in connection with AIDS; improvement in muscle strength, mobility, maintenance of skin thickness, metabolic homeostasis and renal homeostasis in the frail elderly, stimulation of osteoblasts, bone remodelling and cartilage growth; regulation of food intake; stimulation of the immune system in companion animals and treatment of disorder of aging in companion animals, promoting growth in livestock and stimulation of wool growth in sheep, increasing milk production in livestock, treatment of metabolic syndrome (syndrome X), treatment of insulin resistance, including NIDDM, in mammals, e.g. humans, treatment of insulin resistance in the heart, improvement of sleep quality and correction of the relative hyposomatotropism of senescence due to high increase in REM sleep and a decrease in REM latency, treatment of hypothermia, treatment of frailty associated with ageing, treatment of congestive heart failure, treatment of hip fractures, treatment of immune deficiency in individuals with a depressed T4/T8 cell ratio, treatment of muscular atrophy, treatment of musculoskeletal impairment in elderly, enhancing the activity of protein kinase B (PKB), improvement of the overall pulmonary function, treatment of sleep disorders, treatment of growth retardation in connection with asthma, treatment of growth retardation in connection with juvenile rheumatic arthritis, and treatment of growth retardation in connection with cystic fibrosis.

For the above indications the dosage will vary depending on the mode of administration and on the therapy desired. However, generally dosage levels between 0.0001 and 100 mg/kg body weight daily are administered to patients and animals to obtain effective release of endogenous growth hormone. Moreover the compound of the present invention has no or substantially no side-effects, when administered in the above dosage levels, such side-effects being e.g. release of LH, FSH, TSH, ACTH, vasopressin, oxytocin, cortisol and/or prolactin. Usually, dosage forms suitable for oral, nasal, pulmonal or transdermal administration comprise from about 0.0001 mg to about 100 mg, preferably from about 0.001 mg to about 50 mg of the compounds of the present invention admixed with a pharmaceutically acceptable carrier or diluent.

Optionally, the pharmaceutical composition of the invention may comprise the compound of the present invention combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compound of the present invention, it may be useful in vitro tools for investigating the regulation of growth hormone release.

The compound of the present invention may also be a useful in vivo tool for evaluating the growth hormone releasing capability of the pituitary. For example, serum samples taken before and after administration of the compound to humans can be assayed for growth hormone. Comparison of the growth hormone in each serum sample would directly determine the ability of the patient's pituitary to release growth hormone.

The compound of the present invention may be administered to commercially important animals to increase their rate and extent of growth, and to increase milk production.

A further use of the compound of the present invention is in combination with other secretagogues such as GHRP (2 or 6), GHRH and its analogues, growth hormone and its analogues or somatomedins including IGF-1 and IGF-2.

Pharmacological Methods

The compound of the present invention may be evaluated in vitro for its efficacy and potency to release growth hormone in rat pituitary primary cultures, and such evaluation may be performed as described below.

The isolation of rat pituitary cells is a modification of O. Sartor et al., *Endocrinology* 116, 1985, pp. 952–957. Male albino Sprague-Dawley rats (250 +/−25 grams) were purchased from Mollegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in ice-cold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 mg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/l dexamethasone (Sigma D-4902) pH 7.3, to a density of $2 \times 10^5$ cells/ml. The cells were seeded into microtiter plates (Nunc, Denmark), 200 ml/well, and cultured for 3 days at 37° C. and 8% $CO_2$.

Compound Testing

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

The compound was tested in doses ranging from 10 pM to 100 mM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

The compounds of the present invention may be evaluated for its metabolic stability using the procedure described below:

The compound is dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4-10, Angiotensin 1-14 and Glucagon) have been included in the stability tests in order to verify the ability of the various solutions to degrade peptides.

Standard peptides (angiotensin 1-14, ACTH 4-10 and glucagon) were purchased from Sigma, Mo., USA)

Enzymes (trypsin, chymotrypsin, elastase aminopeptidase M and carboxypeptidase Y and B) were all purchased from Boehringer Mannheim GmbH (Mannheim, Germany)

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compound (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy-peptidase mix | Pan. Enzyme mix |
|---|---|---|---|
| Standards | | | |
| ACTH 4-10 | 1124.5/562.8 | + | − |
| Glucagon | 3483/871.8 | − | − |
| Insulin (B23-29) | 859.1/430.6 | − | − |
| Angiotensin 1-14 | 1760.1/881.0 | − | − |
| GHRP-2 | 817.4/409.6 | − | − |
| GHRP-6 | 872.6/437.4 | − | − |

+: Stable (less than 20% decrease in SIM signal after 24 h in degradation solution)
−: Unstable (more than 20% decrease in SIM signal after 24 h in degradation solution)

Pharmacokinetic Methods

The compound of the present invention may be evaluated for its oral bioavailability, and such evaluation may be performed as described below.

The pharmacokinetics of the compound can be investigated in fasted Beagle dogs.

Intravenous and oral administration of the test compound, in 5% glucose solution, was separated by a one weeks washout.

Blood samples were collected immediately before drug administration (time zero) and than 0.08, 0.25, 0.50, 0.75, 1.0, 1.5, 2.0, 3.0, 4.0, 5.0, and 6.0 hours after administration.

The plasma samples were stored frozen (<−18° C.) pending analysis.

An HPLC method with solid phase extraction and UV detection was used for the quantification of the compound in plasma.

The compound of the present invention has an oral availability of about 50%.

The pharmacokinetic parameters for compounds were calculated by non-compartmental methods using the PC based pharmacokinetic software WinNonlin, version 1.1 (Scientific Consulting Inc., Apex, N.C., USA).

EXAMPLES

The process for preparing the compound of the present invention and preparations containing the compound is further illustrated in the following examples, which however, are not to be construed as limiting.

The structures of the compound is confirmed by either High Performance Liquid Chromatography (HPLC), nuclear magnetic resonance (NMR, Bruker 400 MHz) or Liquid Chromatography-Mass Spectrometry (LC-MS). NMR shifts (d) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se. The methanol/ammonia solution used is a 10% ammonia solution in methanol.

HPLC-Analysis
Method A1

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% acetonitrile in a buffer consisting of 0.1 M ammonium sulfate, which was adjusted to pH 2.5 with 4M sulfuric acid. after injection the sample was eluted by a gradient of 5% to 60% acetonitrile in the same buffer during 50 min.

Method B1

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% (acetonitrile+0.1% TFA) in an aqueous solution of TFA in water (0.1%) After injection the sample was eluted by a gradient of 5% to 60% (acetonitrile+0.1% TFA) in the same aqueous buffer during 50 min.

Method h8

The RP-analysis was performed using UV detections at 214 and 254 nm on a 218TP54 4.6 mm×150 mm C-18 silica column, which was eluted at 1 mL/min at 42° C. The column was equilibrated with 5% acetonitrile, 85% water and 10% of a solution of 0.5% trifluoroacetic acid in water and eluted by a linear gradient from 5% acetonitrile, 85% water and 10% of a solution of 0.5% trifluoroacetic acid to 90% acetonitrile and 10% of a solution of 0.5% trifluoroacetic acid over 15 min.

Chirale HPLC

The Chiral HPLC was performed using UV detections at 225 and 254 nm on a 4.6 mm×250 mm Chiracel OJ column fitted with a 4.6 mm×80 mm Chiracel OJ precolumn (both from Daicel Chemical Industries, LTD), which were eluted at 0,7 mL/min at room temperature. The sample was eluted by an isocratic eluent of heptane(92):iPrOH(8):TFA(0,1).

LC-MS-Analysis

The LC-MS analyses were performed on a PE Sciex API 100 LC/MS System using a Waters® 3 mm×150 mm 3.5 m C-18 Symmetry column and positive ionspray with a flow rate of 20 ml/min. The column was eluted with a linear gradient of 5–90% acetonitrile, 85–0% water and 10% trifluoroacetic acid (0.1%)/ water in 15 min at a flow rate of 1 ml/min.

Abbreviations
TLC: thin layer chromatography
DMSO: dimethylsulfoxide
min: minutes
h: hours
Boc: tert butyloxycarbonyl
DMF: dimethylformamide
THF: tetrahydrofuran
EDAC: N-ethyl-N'-dimethylaminopropylcarbodiimide hydrochloride
HOAt: 1-hydroxy-7-azabenzotriazole
DIEA: diisopropylethylamine
TFA: trifluoroacetic acid
Building blocks N-methylated aminoacids used in the following examples were prepared as in Can. J. Chem. 1977, 55, 906.

Formic Acid N',N'-dimethylhydrazide

A mixture of 50 ml of Methylformate and 50 ml of 1,1-Dimethylhydrazine was stirred for 3 days at room temperature. Concentrated in vacuo to form crystals which was stirred in EtOH(5):heptane(95), cooled in a refrigerator overnight and filtered: 50,7 g (575 mmol) (Yield: 88%)

N,N,N'-Trimethylhydrazine, Dihydrochloride

A 2-L three-neck round-bottom flask equipped with a magnetic stirrer and addition funnel was charged with 20,4 g of LiAlH₄, evacuated and flushed with nitrogen. The addition funnel was then equipped with a nitrogen bubbler and 250 ml of dry tetrahydrofurane was added slowly (exothermic). The grey suspension was stirred vigorously and a solution of 40,0 g of formic acid N',N'-dimethylhydrazide in 250 ml of dry tetrahydrofurane was added dropwise over 1 hour. Stirred overnight at room temperature. The reaction was monitored by TLC (CH₂Cl₂ (100):MeOH(10):NH₃(1)).

Another 2-L three-neck round-bottom flask equipped with a dry-ice-condenser was charged with 350 ml of 4,8 M HCl/CH₃OH and placed in a dry-ice-bath (−70° C.). It was then connected to the reaction flask via a vigreux-condenser, and the reaction flask was placed in an oil-bath. A mixture of 200 ml of tetrahydrofurane and 200 ml of MeOH was added carefully to the reaction. Distillation of product and solvent was accomplished by slowly heating to 130° C., resulting in collection of a crystallinic dihydrochloride-salt of trimethylhydrazine (at −70° C.). The dry-ice-bath was removed and temperature allowed to rise to room temperature. Concentration in vacuo afforded a thin colorless oil which was dried overnight using a high vacuum pump: 45,2 g (309 mmol) (Yield: 68%). The very hygroscopic product was kept under nitrogen.

Other starting materials can be purchased from Aldrich.

Example 1

A procedure for the preparation of the compound which is either 2-Amino-N-[(1R)-2-[(3R)-3-benzyl-3-(N,N',N'-trimethylhydrazinocarbonyl)piperidin-1-yl]-1-(1H-indol-3-ylmethyl)-2-oxoethyl]-2-methylpropionamide

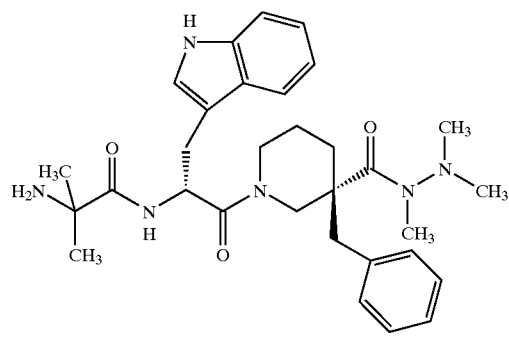

or
2-Amino-N-[(1R)-2-[(3S)-3-benzyl-3-(N,N',N'-trimethylhydrazinocarbonyl)piperidin-1-yl]-1-(1H-indol-3-ylmethyl)-2-oxoethyl]-2-methylpropionamide

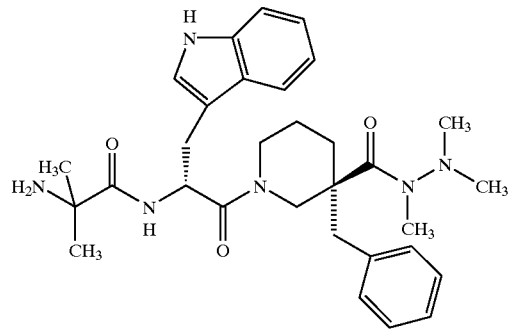

Step a

Piperidine-1,3-dicarboxylic acid 1-tert-butyl ester 3-ethyl ester

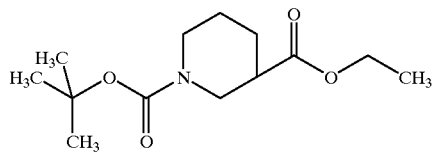

A one-necked round-bottom flask (1l) equipped with a magnetic stirrer and addition funnel was charged with NaOH-pellets (15,6 g), tetrahydrofuran (400 ml) and ethylnipecotate (50 ml, 324 mmol). To the stirred mixture at room temperature was added dropwise a solution of Boc₂O (84,9 g, 389 mmol) dissolved in tetrahydrofuran (150 ml) (1 hour, precipitation of white solid, NaOH-pellets dissolved, exoterm). The mixture was stirred overnight at room temperature. The mixture was added to EtOAc (500 ml) and H₂O (2000 ml), and the aqueous layer was re-extracted with EtOAc (2×500 ml) and the combined organic layers were washed with brine (100 ml), dried over MgSO₄, filtered and concentrated in vacuo to afford piperidine-1,3-dicarboxylic acid 1-tert-butyl ester 3-ethyl ester (82,5 g) as a thin yellow oil.

¹H-NMR (300 MHz, CDCl₃): δ1,25 (t, 3H, CH₃); 1,45 (s, 9H, 3×CH₃); 2,05 (m, 1H); 2,45 (m, 1H); 2,85 (m, 1H); 3,95 (d (broad), 1H); 4,15 (q, 2H, CH₂)

Step b

3-Benzylpiperidine-1,3-dicarboxylic acid 1-tert-butyl ester 3-ethyl ester (racemic mixture)

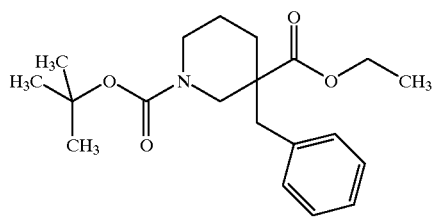

A three-necked round-bottom flask (2 l) equipped with a magnetic stirrer, thermometer, nitrogen bubbler and addition funnel was evacuated, flushed with nitrogen, charged with anhydrous tetrahydrofuran (500 ml) and cooled to −70° C. Then lithium diisopropylamine (164 ml of a 2,0 M solution in tetrahydrofuran, 327 mmol) was added. To the stirred solution at −70° C. was added dropwise over 45 min. a solution of piperidine-1,3-dicarboxylic acid 1-tert-butyl ester 3-ethyl ester (80 g, 311 mmol) in anhydrous tetrahydrofuran (50 ml) (temperature between −70° C. and −60° C., clear red solution). The mixture was stirred for 20 min. and followed by dropwise addition over 40 min. of a solution of benzylbromide (37 ml, 311 mmol) in anhydrous tetrahydrofuran (250 ml) (temperature between −70° C. and −60° C.). The mixture was stirred for 1 hour at −70° C., and then left overnight at room temperature (pale orange). The reaction mixture was concentrated in vacuo to approx. 300 ml, transferred to a separating funnel, diluted with CH₂Cl₂ (900 ml) and washed with H₂O (900 ml). Due to poor separation the aqueous layer was re-extracted with CH₂Cl₂ (200 ml), the combined organic layers were washed with aqueous NaHSO₄ (200 ml, 10%), aqueous NaHCO₃ (200 ml, saturated), H₂O (200 ml), brine (100 ml), dried over MgSO₄, filtered and concentrated in vacuo to afford an oil, which was dissolved in EtOAc(1):heptane(10) and aged overnight. The solids formed was removed by filtration, washed with heptane and dried in vacuo to give a racemic mixture of 3-benzylpiperidine-1,3-dicarboxylic acid 1-tert-butyl ester 3-ethyl ester (81,4 g).

HPLC (h8): Rt=15,79 min. LC-MS: Rt=7,67 min. (m+1)=348,0

Step c

3-Benzylpiperidine-1,3-dicarboxylic acid 1-tert-butyl ester (racemic mixture)

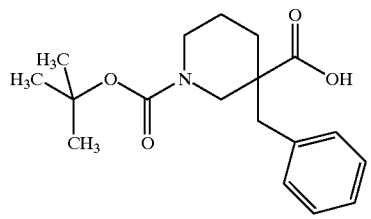

3-Benzylpiperidine-1,3-dicarboxylic acid 1-tert-butyl ester 3-ethyl ester (81 g, 233 mmol) was dissolved in EtOH (400 ml) and NaOH (400 ml, 16% aqueous solution) in a one neck round-bottom flask (1 L) equipped with a condenser and a magnetic stirrer. The mixture was refluxed for 10 h under nitrogen, and cooled to room temperature, concentrated in vacuo to approx. 600 ml (precipitation of a solid), diluted with H$_2$O (400 ml), cooled in an icebath, and under vigorous stirring acidified with 4 M H$_2$SO$_4$ until pH=3 (final temperature: 28° C.). The mixture was extracted with EtOAc (2×700 ml), and the combined organic layers were washed with brine (200 ml), dried over MgSO$_4$, filtered and concentrated in vacuo to afford an oil, which was dissolved in EtOAc(1):heptane(10) and aged overnight. The crystals formed were removed by filtration, washed with heptane and dried in vacuo to give a racemic mixture of 3-benzylpiperidine-1,3-dicarboxylic acid 1-tert-butyl ester (66,0 g)

HPLC (h8): Rt=12,85 min. LC-MS: Rt=5,97 min. (m+1)=320,0

Chirale HPLC (Chiracel OJ, heptane(92):iPrOH(8):TFA (0,1)): Rt=8,29 min. 46,5% Rt=13,69 min. 53,5%

Step d (3R)-3-Benzylpiperidine-1,3-dicarboxylic acid 1-tert-butyl ester or (3S)-3-Benzylpiperidine-1,3-dicarboxylic acid 1-tert-butyl ester (Resolution of 3-Benzylpiperidine-1,3-dicarboxylic acid 1-tert-butyl ester)

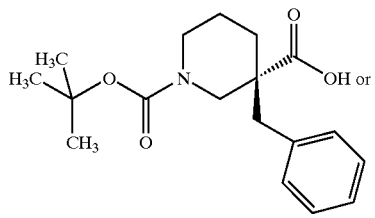

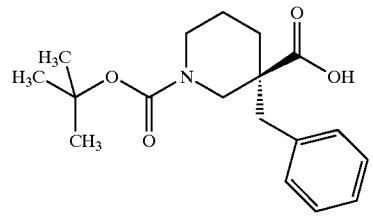

3-Benzylpiperidine-1,3-dicarboxylic acid 1-tert-butyl ester (76 g, 238 mmol) was dissolved in EtOAc (3,0 L) in a one neck flask (5 L) equipped with magnetic stirring. Then H$_2$O (30 ml), R(+)-1-phenethylamine (18,2 ml, 143 mmol) and Et$_3$N (13,2 ml, 95 mmol) were added and the mixture was stirred overnight at room temperature resulting in precipitation of white crystals (41,9 g), which were removed by filtration, washed with EtOAc and dried in vacuo. The precipitate was dissolved in a mixture of aqueous NaHSO$_4$ (300 ml, 10%) and EtOAc (600 ml), layers were separated and the aqueous layer re-extracted with EtOAc (100 ml). The combined organic layers were washed with brine (100 ml), dried over MgSO$_4$ and filtered. The solvent was removed in vacuo to afford a colorless oil, which was dissolved in EtOAc(1):heptane(10) and aged overnight. The crystals that had been formed were removed by filtration, washed with heptane and dried in vacuo to give one compound which is either (3R)-3-benzylpiperidine-1,3-dicarboxylic acid 1-tert-butyl ester or (3S)-3-benzylpiperidine-1,3-dicarboxylic acid 1-tert-butyl ester (27,8 g).

Chirale HPLC (Chiracel OJ, heptane(92):iPrOH(8):TFA (0,1)):Rt=7,96 min. 95,8% ee Step e (3R)-3-Benzyl-3-(N,N',N'-trimethyhydrazinocarbonyl)piperidine-1-carboxylic acid tert-butyl ester or (3S)-3-Benzyl-3-(N,N',N'-trimethylhydrazinocarbonylopiperidine-1-carboxylic acid tert-butyl ester

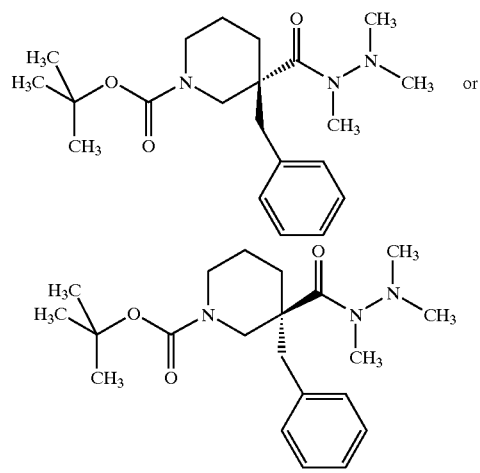

Trimethylhydrazine dihydrochloride (15,3 g, 104 mmol) was suspended in tetrahydrofuran (250 ml) in a one-neck round-bottom flask (1l) equipped with a large magnetic stirrer, and an addition funnel/nitrogen bubbler. The flask was then placed in a water-bath (temp: 10–20° C.), bromo-tris-pyrrolydino-phosphonium-hexafluorophosphate (40,4 g, 86,7 mmol) was added, and under vigorous stirring dropwise addition of diisopropylethylamine (59 ml, 347 mmol). The mixture (with heavy precipitation) was stirred for 5 min., and a solution of the product from step d which is either (3R)-3-benzylpiperidine-1,3-dicarboxylic acid 1-tert-butyl ester or (3S)-3-benzylpiperidine-1,3-dicarboxylic acid 1-tert-butyl ester (27,7 g, 86,7 mmol) in tetrahydrofuran (250 ml) was added slowly over 1,5 hour. The mixture was stirred overnight at room temperature. The reaction was diluted with EtOAc (1000 ml), washed with H$_2$O (500 ml), aqueous NaHSO$_4$, (200 ml, 10%), aqueous NaHCO$_3$ (200 ml, saturated), brine (200 ml), dried over MgSO$_4$, filtered and concentrated in vacuo to afford a thin orange oil. The mixture was dissolved in EtOAc (300 ml), added to SiO$_2$ (150 g) and concentrated in vacuo to a dry powder which was applied onto a filter packed with SiO$_2$ (150 g), washed with heptan (1l) and the desired compound was liberated with EtOAc (2,5l). After concentration in vacuo, the product which is either (3R)-3-benzyl-3-(N,N',N'-trimethylhydrazinocarbonyl)-piperidine-1-carboxylic acid tert-butyl ester or (3S)-3-benzyl-3-(N,N',N'-trimethylhydrazinocarbonyl)-piperidine-1-carboxylic acid tert-butyl ester (49 g) as an orange oil was obtained.

HPLC (h8): Rt=14,33 min.

Step f (3R)-3-Benzyl-piperidine-3-carboxylic acid trimethylhydrazide or (3S)-3-Benzyl-piperidine-3-carboxylic acid trimethylhydrazide

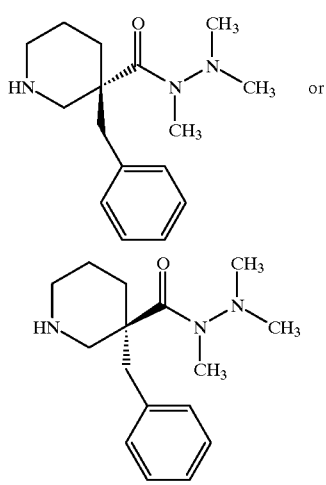

The product from step e which is either (3R)-3-Benzyl-3-(N,N',N'-trimethylhydrazinocarbonyl)-piperidine-1-carboxylic acid tert-butyl ester or (3S)-3-Benzyl-3-(N,N',N'-trimethylhydrazinocarbonyl)-piperidine-1-carboxylic acid tert-butyl ester (56,7 g, 100,9 mmol) was dissolved in EtOAc (500 ml) (clear colorless solution) in a one-neck roundbottom flask (2L) equipped with magnetic stirring. The flask was then placed in a waterbath (temp: 10–20° C.), and HCl-gas was passed through the solution for 5 min. (dust-like precipitation). After stirring for 1 hour (precipitation of large amount of white crystals), the solution was flushed with N$_2$ to remove excess of HCl. The precipitate was removed by gentle filtration, washed with EtOAc (2×100 ml), and dried under vacuum at 40° C. overnight to give the product which is either (3R)-3-benzyl-piperidine-3-carboxylic acid trimethylhydrazide or (3S)-3-benzyl-piperidine-3-carboxylic acid trimethylhydrazide (37,0 g).

HPLC (h8): Rt=7,84 min.

Step g

[(1R)-2-[Benzyl-3-(N,N',N'-trimethylhydrazinocarbonyl)piperidin-1-yl]-1-((1H-indol-3-yl)methyl)-2-oxoethyl]carbamic acid tert-butyl ester or [(1R)-2-[(3S)-3-Benzyl-3-(N,N',N'-trimethylhydrazinocarbonyl)piperidin-1-yl]-1-((1H-indol-3-yl)methyl)-2-oxoethyl]carbamic acid tert-butyl ester

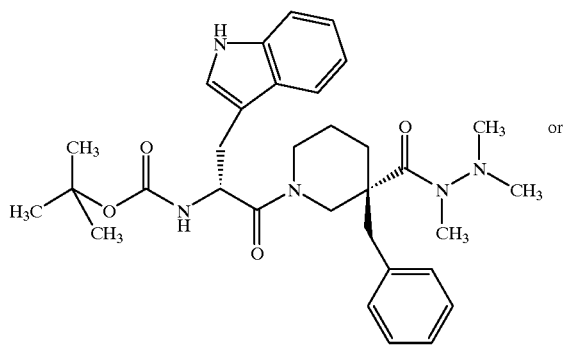

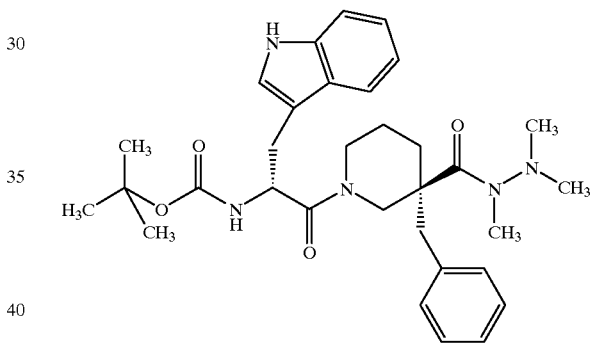

Boc-D-Trp-OH (32,3 g, 106 mmol) was dissolved in dimethylacetamide (250 ml) in a one-neck roundbottom flask (500 ml) equipped with a magnetic stirrer and a nitrogen bubbler. The solution was cooled to 0–5° C. and 1-hydroxy-7-azabenzotriazole (14,4 g,106 mmol), 1-ethyl-3-(3-dimethylaminopropyl)carbodiimid hydrochloride (20,3 g, 106 mmol), N-methylmorpholine (11,6 ml, 106 mmol) were added. After stirring for 20 min. at 0–5° C. the product from step f which is either (3R)-3-benzyl-piperidine-3-carboxylic acid trimethylhydrazide or (3S)-3-benzyl-piperidine-3-carboxylic acid trimethylhydrazide (37,0 g, 106 mmol) and N-methylmorpholine (24,4 ml, 223 mmol) were added. The reaction was stirred overnight at room temperature. The mixture was then added to EtOAc (750 ml) and washed with aqueous NaHSO$_4$ (300 ml, 10%). The layers were allowed to separate, and the aqueous layer was re-extracted with EtOAc (500 ml). The combined organic layers were washed with H$_2$O (100 ml), aqueous NaHCO$_3$ (300 ml, saturated), H$_2$O (100 ml), brine (300 ml), dried over MgSO$_4$, filtered and concentrated in vacuo to afford the product which is either [(1R)-2-[(3R)-3-benzyl-3-(N,N',N'-trimethylhydrazinocarbonyl)piperidin-1-yl]-1-((1H)-indol-3-yl)methyl)-2-oxoethyl]carbamic acid tert-butyl ester or [(1R)-2-[(3S)-3-benzyl-3-(N,N',N'- trimethylhydrazinocarbonyl)piperidin-1-yl]-1-((1H-indol-3-yl)methyl)-2-oxoethyl]carbamic acid tert-butyl ester (56,7 g) as an orange oil.

HPLC (h8): Rt=14,61 min. LC-MS: Rt=7,35 min. (m+1)= 562,6

Step h

1-[(2R)-2-Amino-3-(1H-indol-3-yl)propionyl]-(3R)-3-benzylpiperidine-3-carboxylic acid trimethylhydrazide or 1-[(2R)-2-Amino-3-(1H-indol-3-yl)propionyl]-(3S)-3-benzylpiperidine-3-carboxylic acid trimethylhydrazide

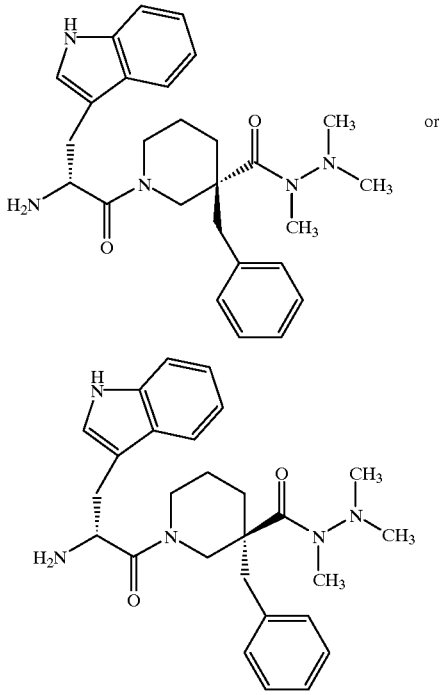

The product from step g which is either [(1R)-2-[(3R)-3-benzyl-3-(N,N',N'-trimethylhydrazinocarbonyl)piperidin-1-yl]-1-((1H-indol-3-yl)methyl)-2-oxoethyl]carbamic acid tert-butyl ester or [(1R)-2-[(3R)-3-benzyl-3-(N,N',N'-trimethylhydrazinocarbonyl)piperidin-1-yl]-1-((1H-indol-3-yl)methyl)-2-oxoethyl]carbamic acid tert-butyl ester (56,7 g, 100,9 mmol) was dissolved in EtOAc (500 ml) (clear colorless solution) in a one-neck round-bottom flask (2L) equipped with magnetic stirring. The flask was then placed in a water-bath (temp: 10–20° C.), and HCl-gas was passed through the solution for 10 min. (heavy precipitation of oil). The mixture was flushed with $N_2$ to remove excess of HCl and then separated into an oil and an EtOAc-layer. The EtOAc-layer was discarded. The oil was dissolved in $H_2O$ (500 ml), $CH_2Cl_2$ (1000 ml), and solid $Na_2CO_3$ was added until pH>7. The layers were separated, and the organic layer was washed with $H_2O$ (100 ml), brine (100 ml), dried over $MgSO_4$, filtered and concentrated in vacuo to afford the product which is either 1-[(2R)-2-amino-3-(1H-indol-3-yl)propionyl]-(3R)-3-benzylpiperidine-3-carboxylic acid trimethylhydrazide or 1-[(2R)-2-amino-3-(1H-indol-3-yl)propionyl]-(3S)-3-benzylpiperidine-3-carboxylic acid trimethylhydrazide (27 g) as an orange foam.

HPLC (h8): Rt=10,03 min.

Step i

{1-[(1R)-2-](3R)-3-Benzyl-3-(N,N',N'-trimethylhydrazinocarbonyl)piperidin-1-yl-]-1-(1H-indol-3-ylmethyl)-2-oxo-ethylcarbamoyl]-1-methylethyl}carbamic acid tert-butyl ester or {1-(1R)-2-[(3S)-3-Benzyl-3-(N,N',N'-trimethylhydrazinocarbonyl)piperidin-1-yl]-1-(1H-indol-3-ylmethyl)-2-oxo-ethylcarbamoyl]-1-methylethyl}carbamic acid tert-butyl ester

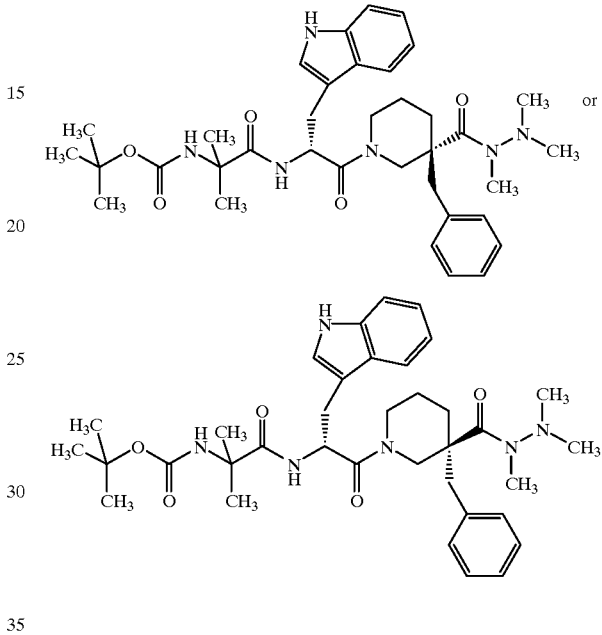

Boc-Aib-OH (11,9 g, 58,4 mmol) was dissolved in dimethylacetamide (125 ml) in a one-neck roundbottom flask (500 ml) equipped with a magnetic stirrer and nitrogen bubbler. To the stirred solution at room temperature were added 1-hydroxy-7-azabenzotriazole (7,95 g, 58,4 mmol), 1-ethyl-3-(3-dimethylaminopropyl)carbodiimid hydrochloride (11,2 g, 58,4 mmol), and diisopropylethylamine (13,0 ml, 75,8 mmol). After 20 min. (yellow with precipitation) a solution of the product from step h which is either 1-[(2R)-2-amino-3-(1H-indol-3-yl)propionyl]-(3R)-3-benzylpiperidine-3-carboxylic acid trimethylhydrazide or 1-[(2R)-2-amino-3-(1H-indol-3-yl)propionyl]-(3S)-3-benzylpiperidine-3-carboxylic acid trimethylhydrazide (27,0 g, 58,4 mmol) in dimethylacetamide (125 ml) was added. The reaction was stirred at room temperature for 3 h. The mixture was added to EtOAc (750 ml) and washed with aqueous $NaHSO_4$ (300 ml, 10%). The layers were allowed to separate, and the aqueous layer was re-extracted with EtOAc (500 ml). The combined organic layers were washed with $H_2O$ (100 ml), aqueous $NaHCO_3$ (300 ml, saturated), $H_2O$ (100 ml), brine (300 ml), dried over $MgSO_4$, filtered and concentrated in vacuo to approx. 500 ml. Then $SiO_2$ (150 g) was added and the remaining EtOAc removed in vacuo to give a dry powder which was applied onto a filter packed with $SiO_2$(150 g), washed with heptan (1 L), and the desired compound was liberated with EtOAc (2,5 L). After concentration in vacuo, the product which is either {1-[(1R)-2-[(3R)-3-benzyl-3-(N,N',N'-trimethylhydrazinocarbonyl)piperidin-1-yl]-1-(1H-indol-3-ylmethyl)-2-oxo-ethylcarbamoyl]-1-methylethyl}carbamic acid tert-butyl ester or {1-[(1R)-2-[(3S)-3-benzyl-3-(N,N',N'-trimethylhydrazinocarbonyl)piperidin-1-yl]-1-(1H--indol-3- ylmethyl)-2-oxo-ethylcarbamoyl]-1-methylethyl}carbamic acid tert-butyl ester 33,9 g as an orange foam was obtained.
HPLC (h8): Rt=14,05 min.

Step j

2-Amino-N-[(1R)-2-[(3R)-3-benzyl-3-(N,N',N'-trimethylhydrazinocarbonyl)piperidin-1-yl]-1-(1H-indol-3-ylmethyl)-2-oxoethyl]-2-methylpropionamide, fumarate or 2-Amino-N-[(1R)-2-[(3S)-3-benzyl-3-(N,N',N'-trimethylhydrazinocarbonyl)piperidin-1-yl]-1-(1H-indol-3-ylmethyl)-2-oxoethyl]2-methylpropionamide, fumarate

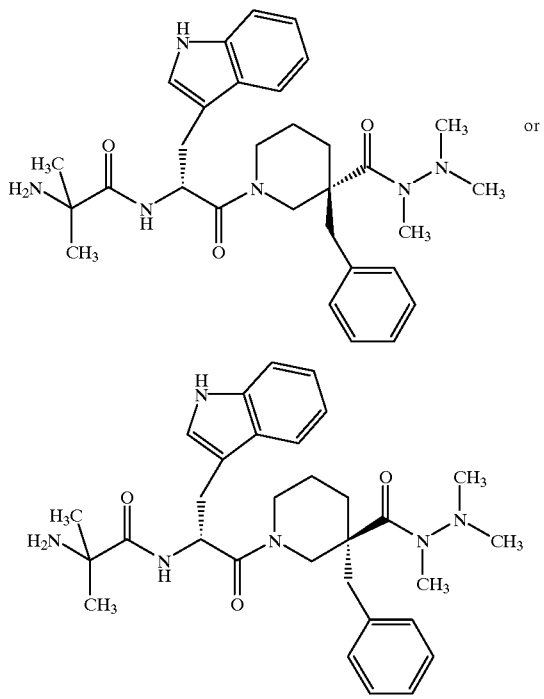

The product from step i which is either {1-[(1R)-2-[(3R)-3-benzyl-3-(N,N',N'-trimethylhydrazinocarbonyl)piperidin-1-yl]-1-(1H-indol-3-ylmethyl)-2-oxo-ethylcarbamoyl]-1-methylethyl}carbamic acid tert-butyl ester or {1-[(1R)-2-[(3S)-3-benzyl-3-(N,N',N'-trimethylhydrazinocarbonyl)piperidin-1-yl]-1-(1H-indol-3-ylmethyl)-2-oxo-ethylcarbamoyl]-1-methylethyl}carbamic acid tert-butyl ester (23,8 g, 36,8 mmol) was dissolved in of EtOAc (800 ml) (clear yellow solution) in a one neck round-bottom flask (1 L) equipped with magnetic stirring. The flask was then placed in a water-bath (temp: 10–20° C.), and HCl-gas was passed through the solution for 5 min. (dust-like precipitation). After stirring for 1 hour (precipitation of large amount of yellow powder), the solution was flushed with $N_2$ to remove excess of HCl. The precipitate was removed by gentle filtration and dried under vacuum at 40° C. overnight.

The non-crystallinic precipitate was dissolved in $H_2O$ (500 ml) and washed with EtOAc (100 ml). Then $CH_2Cl_2$ (1000 ml) and solid $Na_2CO_3$ was added until pH>7. The 2 layers were separated, and the aqueous layer was re-extracted with $CH_2Cl_2$ (200 ml). The combined organic layers were washed with brine (100 ml), dried over $MgSO_4$ and filtered. The solvent was evaporated under reduced pressure and redissolved in EtOAc (500 ml) in a one neck round-bottom flask (1 L) equipped with magnetic stirring. A suspension of fumaric acid (3,67 g) in isopropanol (20 ml) and EtOAc (50 ml) was slowly added (5 min.), which resulted in precipitation of a white crystallinic salt. After 1 hour the precipitation was isolated by filtration and dried overnight in vacuum at 40° C. to give the fumarate salt of the compound which is either 2-amino-N-[(1R)-2-[(3R)-3-benzyl-3-(N,N',N'-trimethylhydrazinocarbonyl)piperidin-1-yl]-1-(1H-indol-3-ylmethyl)-2-oxoethyl]-2-methylpropionamide or 2-amino-N-[(1R)-2-[(3S)-3-benzyl-3-(N,N',N'-trimethylhydrazinocarbonyl)piperidin-1-yl]-1-(1H-indol-3-ylmethyl)-2-oxoethyl]-2-methylpropionamide (13,9 g) as a white powder HPLC (A1): Rt=33,61 min. HPLC (B1): Rt=34,62 min. LC-MS: Rt=5,09 min. (m+1)=547,4

What is claimed is:

1. A compound 2-Amino-N-[(1R)-2-[(3R)-3-benzyl-3-(N,N',N'-trimethylhydrazinocarbonyl)piperidin-1-yl]-1-(1H-indol-3-ylmethyl)-2-oxoethyl]-2-methylpropionamide, having the following structure:

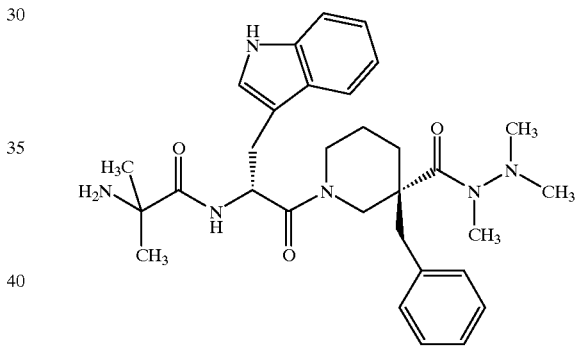

or a pharmaceutically acceptable salt thereof.

2. A pharmaceutical composition comprising, as an active ingredient, the compound of claim 1, together with a pharmaceutically acceptable carrier or diluent.

3. A method of stimulating the release of growth hormone from the pituitary of a mammal, the method comprising administering to said mammal an effective amount of the compound of claim 1.

4. A method of increasing growth, milk production, wool production or treating a disorder wherein increased level of growth hormone is desired, comprising administering to a subject in need thereof, an endogenous growth hormone releasing effective amount of a compound of claim 1.

* * * * *